United States Patent
Stokes et al.

[11] Patent Number: 5,931,823
[45] Date of Patent: Aug. 3, 1999

[54] HIGH PERMEABILITY LINER WITH IMPROVED INTAKE AND DISTRIBUTION

[75] Inventors: Ty Jackson Stokes, Suwanee; Darryl Franklin Clark, Alpharetta; Eugenio Go Varona, Marietta, all of Ga.

[73] Assignee: Kimberly-Clark Worldwide, Inc., Neenah, Wis.

[21] Appl. No.: 08/829,273

[22] Filed: Mar. 31, 1997

[51] Int. Cl.⁶ ........................................... A61F 13/15
[52] U.S. Cl. ........................................... 604/358; 604/380
[58] Field of Search ........................... 604/358, 378–380

[56] References Cited

U.S. PATENT DOCUMENTS

| | | |
|---|---|---|
| 3,260,778 | 7/1966 | Walton . |
| 3,276,944 | 10/1966 | Levy . |
| 3,338,992 | 8/1967 | Kinney . |
| 3,341,394 | 9/1967 | Kinney . |
| 3,423,266 | 1/1969 | Davies et al. . |
| 3,464,876 | 9/1969 | Barb . |
| 3,484,330 | 12/1969 | Sokolowski et al. . |
| 3,502,538 | 3/1970 | Petersen . |
| 3,502,763 | 3/1970 | Hartmann . |
| 3,507,943 | 4/1970 | Such et al. . |
| 3,542,615 | 11/1970 | Dobo et al. . |
| 3,668,054 | 6/1972 | Stumpf . |
| 3,692,618 | 9/1972 | Dorschner et al. . |
| 3,694,867 | 10/1972 | Stumpf . |
| 3,705,063 | 12/1972 | Stumpf . |
| 3,705,065 | 12/1972 | Stumpf . |
| 3,708,361 | 1/1973 | Stumpf . |
| 3,709,768 | 1/1973 | Stumpf . |
| 3,720,554 | 3/1973 | Stumpf . |
| 3,802,817 | 4/1974 | Matsuki et al. . |
| 3,849,241 | 11/1974 | Butin et al. . |
| 3,855,046 | 12/1974 | Hansen et al. ........................... 161/150 |
| 3,863,304 | 2/1975 | Brumlik . |
| 3,922,455 | 11/1975 | Brumlik . |
| 3,927,443 | 12/1975 | Brumlik . |
| 4,035,219 | 7/1977 | Cumbers . |
| 4,068,036 | 1/1978 | Stanistreet . |
| 4,082,886 | 4/1978 | Batterworth et al. . |

(List continued on next page.)

FOREIGN PATENT DOCUMENTS

| | | |
|---|---|---|
| 0 091 419 | 10/1983 | European Pat. Off. . |
| 0 105 729 | 4/1984 | European Pat. Off. . |
| 0 138 549 | 4/1985 | European Pat. Off. . |
| 0 151 348 | 8/1985 | European Pat. Off. . |
| 0 169 868 | 2/1986 | European Pat. Off. . |
| 0 173 058 | 3/1986 | European Pat. Off. . |
| 0 193 938 | 9/1986 | European Pat. Off. ........ B32B 27/10 |
| 0 211 564 | 2/1987 | European Pat. Off. ........ A44B 18/00 |
| 0 237 213 | 9/1987 | European Pat. Off. ........ B65D 65/40 |

(List continued on next page.)

OTHER PUBLICATIONS

Patent Abstracts of Japan/Pub. No. 03241079/Pub. Date Oct. 28, 1991.
Patent Abstracts of Japan/Pub. No. 08322881/Pub. Date Dec. 10, 1996.
"Polymer Blends and Composites," John A. Manson and Leslie H. Sperling, Plenum Press, New York and London, ISBN 0–306–30831–2.
3M Mechanical Closure Systems (Personal Care and Related Products).
Patent Abstracts of Japan/Pub. No. 07313213/Pub. Date May 12, 1995.

*Primary Examiner*—John G. Weiss
*Assistant Examiner*—Dennis Ruhl
*Attorney, Agent, or Firm*—James B. Robinson

[57] ABSTRACT

There is provided a absorbent material for personal care products which is made from wettable fibers of at most 40 microns in diameter which are made into a web and where the web has controlled spaces in the side away from a wearer point unbonded bonding pattern. The web will accept a liquid insult of 50 ml with a runover/run-through percentage ratio of less than 1.5.

10 Claims, 5 Drawing Sheets

U.S. PATENT DOCUMENTS

| | | |
|---|---|---|
| 4,100,324 | 7/1978 | Anderson et al. . |
| 4,115,620 | 9/1978 | Gupta et al. . |
| 4,162,344 | 7/1979 | Rones . |
| 4,170,680 | 10/1979 | Cumbers . |
| 4,172,172 | 10/1979 | Suzuki et al. . |
| 4,189,338 | 2/1980 | Ejima et al. . |
| 4,211,819 | 7/1980 | Kunimune et al. . |
| 4,214,582 | 7/1980 | Patel . |
| 4,258,094 | 3/1981 | Benedyk . |
| 4,269,888 | 5/1981 | Ejima et al. . |
| 4,290,174 | 9/1981 | Kalleberg . |
| 4,297,404 | 10/1981 | Nguyen . |
| 4,306,929 | 12/1981 | Menikheim et al. . |
| 4,315,881 | 2/1982 | Nakajima et al. . |
| 4,323,534 | 4/1982 | DesMarais . |
| 4,340,563 | 7/1982 | Appel et al. . |
| 4,355,066 | 10/1982 | Newman . |
| 4,374,888 | 2/1983 | Bornslaeger . |
| 4,391,869 | 7/1983 | Cook et al. . |
| 4,402,690 | 9/1983 | Redfern . |
| 4,469,540 | 9/1984 | Furukawa et al. . |
| 4,573,991 | 3/1986 | Pieniak et al. . |
| 4,587,152 | 5/1986 | Gleichenhagen et al. . |
| 4,592,943 | 6/1986 | Cancian et al. . |
| 4,596,568 | 6/1986 | Flug . |
| 4,600,618 | 7/1986 | Raychok, Jr. et al. . |
| 4,631,933 | 12/1986 | Carey, Jr. . |
| 4,652,484 | 3/1987 | Shiba et al. . |
| 4,663,220 | 5/1987 | Wisneski et al. . |
| 4,668,552 | 5/1987 | Scott . |
| 4,695,500 | 9/1987 | Dyer et al. . |
| 4,699,622 | 10/1987 | Toussant et al. . |
| 4,704,116 | 11/1987 | Enloe . |
| 4,704,117 | 11/1987 | Mitchell . |
| 4,707,893 | 11/1987 | Hashizume et al. . |
| 4,739,635 | 4/1988 | Conley et al. . |
| 4,761,318 | 8/1988 | Ott et al. . |
| 4,774,124 | 9/1988 | Shimalla et al. . |
| 4,795,668 | 1/1989 | Krueger et al. . |
| 4,818,464 | 4/1989 | Lau . |
| 4,834,738 | 5/1989 | Kielpikowski et al. . |
| 4,846,815 | 7/1989 | Scripps . |
| 4,869,724 | 9/1989 | Scripps . |
| 4,883,707 | 11/1989 | Newkirk . |
| 4,891,957 | 1/1990 | Strack et al. . |
| 4,910,062 | 3/1990 | Zinke et al. . |
| 4,973,326 | 11/1990 | Wood et al. . |
| 4,994,054 | 2/1991 | Pigneul et al. . |
| 5,032,122 | 7/1991 | Noel et al. . |
| 5,057,368 | 10/1991 | Largman et al. . |
| 5,069,970 | 12/1991 | Largman et al. . |
| 5,093,422 | 3/1992 | Himes . |
| 5,108,820 | 4/1992 | Kaneko et al. . |
| 5,108,827 | 4/1992 | Gessner . |
| 5,119,643 | 6/1992 | Conley et al. . |
| 5,256,231 | 10/1993 | Gorman et al. . |
| 5,277,976 | 1/1994 | Hogle et al. . |
| 5,294,478 | 3/1994 | Wanek et al. . |
| 5,304,599 | 4/1994 | Himes . |
| 5,326,612 | 7/1994 | Goulait . |
| 5,336,552 | 8/1994 | Strack et al. . |
| 5,369,853 | 12/1994 | Okawa et al. . |
| 5,380,313 | 1/1995 | Goulait et al. . |
| 5,382,400 | 1/1995 | Pike et al. . |
| 5,407,439 | 4/1995 | Goulait . |
| 5,418,045 | 5/1995 | Pike et al. . |
| 5,466,410 | 11/1995 | Hills . |
| 5,614,281 | 3/1997 | Jackson et al. . |
| 5,695,377 | 12/1997 | Triebes et al. ........................ 442/369 |

FOREIGN PATENT DOCUMENTS

| | | | |
|---|---|---|---|
| 0 240 213 | 10/1987 | European Pat. Off. | ........ A61F 13/15 |
| 0 241 234 | 10/1987 | European Pat. Off. | ........... C08J 5/18 |
| 0 252 743 | 1/1988 | European Pat. Off. | ....... D04H 13/00 |
| 0 255 202 | 2/1988 | European Pat. Off. | ....... D03D 27/00 |
| 0 286 409 | 10/1988 | European Pat. Off. | ........ B32B 27/12 |
| 0 289 198 | 11/1988 | European Pat. Off. | ........ A44B 18/00 |
| 0 294 178 | 12/1988 | European Pat. Off. | ........ B32B 27/12 |
| 0 321 234 | 6/1989 | European Pat. Off. | ........ A61F 13/15 |
| 0 330 415 | 8/1989 | European Pat. Off. | ....... D03D 15/00 |
| 0 341 993 | 11/1989 | European Pat. Off. . | |
| 0 360 208 | 3/1990 | European Pat. Off. | ........ B32B 27/08 |
| 0 370 094 | 5/1990 | European Pat. Off. | ......... A47G 9/00 |
| 0 389 611 | 10/1990 | European Pat. Off. | ........ C08L 23/08 |
| 0 393 953 | 10/1990 | European Pat. Off. | ........ A61F 13/60 |
| 0 415 758 | 3/1991 | European Pat. Off. | ........ B32B 27/12 |
| 0 424 855 | 5/1991 | European Pat. Off. | ........ B65D 81/26 |
| 0 443 541 | 8/1991 | European Pat. Off. | .......... B32B 7/00 |
| 0 474 376 | 3/1992 | European Pat. Off. | ........ C08L 23/10 |
| 0 496 894 | 8/1992 | European Pat. Off. | ........ B60R 21/16 |
| 0 497 608 | 8/1992 | European Pat. Off. | ........ B32B 27/06 |
| 0 528 563 | 2/1993 | European Pat. Off. | ........... C09J 7/02 |
| 0 536 323 | 4/1993 | European Pat. Off. | ........ A61F 13/15 |
| 0 539 504 | 5/1993 | European Pat. Off. | ........ A44B 18/00 |
| 0 563 284 | 10/1993 | European Pat. Off. | ........ A44B 18/00 |
| 0 552 810 | 12/1993 | European Pat. Off. | .......... D01F 6/30 |
| 0 575 123 | 12/1993 | European Pat. Off. | ........ C08L 23/08 |
| 0 581 524 | 2/1994 | European Pat. Off. | .......... B32B 5/04 |
| 0 581 570 | 2/1994 | European Pat. Off. | ........ A44B 18/00 |
| 0 608 369 | 8/1994 | European Pat. Off. | ........ C08F 10/00 |
| 0 616 618 | 9/1994 | European Pat. Off. | ...... C08F 210/02 |
| 0 629 151 | 12/1994 | European Pat. Off. | ........ B29C 55/00 |
| 0 633 009 | 1/1995 | European Pat. Off. . | |
| 0 662 988 | 7/1995 | European Pat. Off. | ........ C08L 23/04 |
| 0 672 774 | 9/1995 | European Pat. Off. . | |
| 0 691 366 | 1/1996 | European Pat. Off. | ........... C08J 5/18 |
| 1 552 520 | 9/1979 | United Kingdom . | |
| 2 048 168 | 12/1980 | United Kingdom . | |
| 1 594 444 | 7/1981 | United Kingdom . | |
| 2 105 758 | 3/1983 | United Kingdom . | |
| 2 114 449 | 8/1983 | United Kingdom . | |
| 2 160 586 | 12/1985 | United Kingdom . | |
| 2 279 106 | 12/1994 | United Kingdom . | |
| 87/05953 | 10/1987 | WIPO . | |
| 91/12132 | 8/1991 | WIPO . | |
| 92/01401 | 2/1992 | WIPO . | |
| 92/15444 | 9/1992 | WIPO . | |
| 92/20250 | 11/1992 | WIPO . | |
| 92/20251 | 11/1992 | WIPO . | |
| 93/07210 | 4/1993 | WIPO . | |
| 93/21242 | 10/1993 | WIPO . | |
| 94/07930 | 4/1994 | WIPO . | |
| 94/14855 | 7/1994 | WIPO . | |
| 94/18263 | 8/1994 | WIPO . | |
| 94/28064 | 12/1994 | WIPO . | |
| 95/01250 | 1/1995 | WIPO . | |
| 95/03765 | 2/1995 | WIPO . | |
| 95/04654 | 2/1995 | WIPO . | |
| 95/05418 | 2/1995 | WIPO . | |
| 95 06770 | 3/1995 | WIPO . | |
| 95 07677 | 3/1995 | WIPO . | |
| 95/07677 | 3/1995 | WIPO . | |
| 95/09261 | 4/1995 | WIPO . | |
| 95/11264 | 4/1995 | WIPO . | |

| | | | | | | |
|---|---|---|---|---|---|---|
| 95 25496 | 9/1995 | WIPO . | | 96/11804 | 4/1996 | WIPO . |
| 95/25496 | 9/1995 | WIPO . | | 96/16119 | 5/1996 | WIPO . |
| 95/30708 | 11/1995 | WIPO . | | 96/23838 | 8/1996 | WIPO . |
| 95 33390 | 12/1995 | WIPO . | | 97/23182 | 7/1997 | WIPO . |
| 95/33390 | 12/1995 | WIPO . | | 97/24482 | 7/1997 | WIPO . |

HIGH PERMEABILITY LINER WITH IMPROVED INTAKE AND DISTRIBUTION

FIELD OF THE INVENTION

This invention relates to absorbent articles particularly absorbent structures which are useful in personal care products such as disposable diapers, incontinence guards, child care training pants, or sanitary napkins. More particularly, the invention relates to absorbent articles which have a portion designed for rapid intake and distribution of repeated liquid surges to the remainder of the article.

BACKGROUND OF THE INVENTION

Personal care products are absorbent articles including diapers, training pants, feminine hygiene products such as sanitary napkins, incontinence devices and the like. These products are designed to absorb and contain body exudates and are generally single-use or disposable items which are discarded after a relatively short period of use—usually a period of hours—and are not intended to be washed and reused. Such products usually are placed against or in proximity to the wearer's body to absorb and contain various exudates discharged from the body. All of these products typically include a liquid permeable bodyside liner or cover, a liquid impermeable outer cover or backsheet, and an absorbent structure disposed between the bodyside liner and outer cover. The absorbent structure may include a surge layer subjacent to and in liquid communicating contact with the bodyside liner, and an absorbent core often formed of a blend or mixture of cellulosic pulp fluff fibers and absorbent gelling particles subjacent to and in liquid communicating contact with the surge layer.

Desirably, personal care absorbent articles exhibit low leakage from the product and a dry feel for the wearer. It has been found that urination can occur at rates as high as 15 to 20 milliliters per second and at velocities as high as 280 centimeters per second and that an absorbent garment, such as a diaper, may fail by leaking from the leg or front or back waist areas. The inability of the absorbent product to rapidly uptake liquid can also result in excessive pooling of liquid on the body-facing surface of the bodyside liner before the liquid is taken up by the absorbent structure. Such pooled liquid can wet the wearer's skin and can leak from leg or waist openings of the absorbent article, causing discomfort, potential skin health problems, as well as soiling of the outer clothing or bedding of the wearer.

Leakage and pooling can result from a variety of performance deficiencies in the design of the products, or individual materials within the product. One cause of such problems is an insufficient rate of liquid intake into the absorbent core, which functions to absorb and retain body exudates. The liquid intake of a given absorbent product, therefore, and particularly the bodyside liner and surge materials used in an absorbent product, must meet or exceed the expected liquid delivery rates into the absorbent product. An insufficient intake rate becomes even more detrimental to product performance on second, third, or fourth liquid surges. In addition, leakage may occur due to poor wet product fit that results when multiple insults are stored in the target location and cause sagging and drooping from the wet, heavy retention material structure.

Various approaches have been taken to reduce or eliminate leakage from personal care absorbent articles. For example, physical barriers, such as elasticized leg openings and elasticized containment flaps, have been incorporated into such absorbent products. The amount and configuration of absorbent material in the zone of the absorbent structure in which liquid surges typically occur (sometimes referred to as a target zone) also have been modified.

Other approaches to improving overall liquid intake of absorbent articles have focused on the bodyside liner and its capacity to rapidly pass liquid to the absorbent structure of the absorbent article. Nonwoven materials, including bonded carded webs and spunbond webs, have been widely used as bodyside liners. Such nonwoven materials generally are intended to be sufficiently open and/or porous to allow liquid to pass through rapidly, while also functioning to keep the wearer's skin separate from the wetted absorbent underlying the liner. Attempts to improve the liquid intake of liner materials have included, for example, aperturing the liner material, treating the fibers forming the liner material with surfactants to enhance the wettability of the liner, and altering the durability of such surfactants.

Yet another approach has been to introduce one or more additional layers of material, typically between the bodyside liner and absorbent core, to enhance the liquid intake performance of the absorbent product and to provide separation between the absorbent core and the bodyside liner adjacent the wearer's skin. One such additional layer, commonly referred to as a surge layer, can suitably be formed of thick, lofty nonwoven materials. Surge layers, particularly high loft, high bulk, compression resistant fibrous structures, provide a temporary retention or absorption function for liquid not yet absorbed into the absorbent core, which tends to reduce fluid flowback or wetback from the absorbent core to the liner.

Despite these improvements, the need exists for further improvement in the liquid intake performance of liner materials employed in absorbent articles. In particular, there is a need for liner materials that can rapidly intake and distribute a large portion of a liquid insult. This improved handling is critical for narrow crotch absorbent product designs that utilize less retention storage material in the target region.

The present invention provides a high permeability liner with improved fluid intake and distribution which is very desirable when used in absorbent articles.

SUMMARY OF THE INVENTION

The objects of this invention are achieved by an absorbent nonwoven material for personal care products which is made from wettable fibers of at most 40 microns in diameter which are made into a web and where the web has controlled spaces on the side away from a wearer. The web will accept a liquid insult of 50 ml with a runover/run-through percentage ratio of less than 1.5. Such a web liner may be used in personal care products like diapers, training pants, absorbent underpants, adult incontinence products and feminine hygiene products. Especially of interest are diapers having a narrow crotch, i.e., those having a crotch width of at most 7.6 cm.

DEFINITIONS

Figure 1:
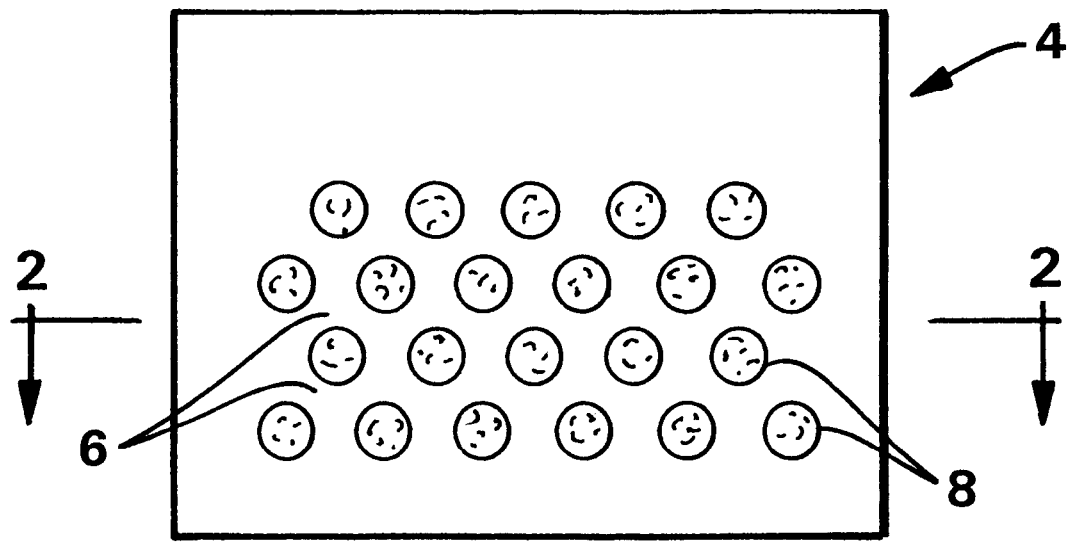
FIG. 1 is a top elevation view of a pattern-unbonded nonwoven fabric.

"Disposable" includes being disposed of after usually a single use and not intended to be washed and reused.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than 90° are designated "nonwettable" or hydrophobic.

"Layer" when used in the singular can have the dual meaning of a single element or a plurality of elements.

"Liquid" means a nongaseous and nonparticulate substance and/or material that flows and can assume the interior shape of a container into which it is poured or placed.

"Liquid communication" means that liquid such as urine is able to travel from one location to another location.

"Longitudinal" and "transverse" have their customary meanings. The longitudinal axis lies in the plane of the article when laid flat and fully extended and is generally parallel to a vertical plane that bisects a standing wearer into left and right body halves when the article is worm. The transverse axis lies in the plane of the article generally perpendicular to the longitudinal axis.

"Particles" refers to any geometric form such as, but not limited to, spherical grains, cylindrical fibers or strands, or the like.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and 5,069,970 and 5,057,368 to Largman et al., which describe fibers with unconventional shapes.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be pulp, superabsorbent particles, cellulose or staple fibers, for example. Coform processes are shown in commonly assigned U.S. Pat. Nos. 4,818,464 to Lau and 4,100,324 to Anderson et al. Webs produced by the coform process are generally referred to as coform materials.

"Conjugate fibers" refers to fibers which have been formed from at least two polymer sources extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. Nos. 5,277,976 to Hogle et al., and 5,069,970 and 5,057,368 to Largman et al., hereby incorporated by reference in their entirety, which describe fibers with unconventional shapes. Polymers useful in forming conjugate fibers include those normally used in the spunbonding and meltblowing processes including various polyolefins, nylons, polyesters, etc.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Bonded carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales which are placed in an opener/blender or picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" is a well known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

As used herein, the term "compaction roll" means a set of rollers above and below the web to compact the web as a way of treating a just produced microfiber, particularly spunbond, web in order to give it sufficient integrity for further processing, but not the relatively strong bonding of secondary bonding processes like through-air bonding, thermal bonding and ultrasonic bonding. Compaction rolls slightly squeeze the web in order to increase its self-adherence and thereby its integrity. Compaction rolls perform this function well but have a number of drawbacks. One such drawback is that compaction rolls do indeed compact the web, causing a decrease in bulk or loft in the web which may be undesirable for the use desired. A second and more serious drawback to compaction rolls is that the web will sometimes wrap around one or both of the rollers, causing a shutdown of the web production line for cleaning of the rollers, with the accompanying obvious loss in production during the down time. A third drawback of compaction rolls is that, if a slight imperfection is produced in formation of the web, such as a drop of polymer being formed into the web, the compaction roll can force the drop into the foraminous belt, onto which most webs are formed, causing an imperfection in the belt and ruining it.

As used herein, the term "hot air knife" or HAK means a process of pre- or primarily bonding a just produced microfiber, particularly spunbond, web in order to give it sufficient integrity, i.e. increase the stiffness of the web, for further processing, but does not mean the relatively strong bonding of secondary bonding processes like TAB, thermal bonding and ultrasonic bonding. A hot air knife is a device which focuses a stream of heated air at a very high flow rate, generally from about 1000 to about 10000 feet per minute (fpm) (305 to 3050 meters per minute), or more particularly from about 3000 to 5000 feet per minute (915 to 1525 m/min.) directed at the nonwoven web immediately after its formation. The air temperature is usually in the range of the melting point of at least one of the polymers used in the web, generally between about 200 and 550° F. (93 and 290° C.) for the thermoplastic polymers commonly used in spunbonding. The control of air temperature, velocity, pressure, volume and other factors helps avoid damage to the web while increasing its integrity. The HAK's focused stream of air is arranged and directed by at least one slot of about ⅛ to 1 inches (3 to 25 mm) in width, particularly about ⅜ inch (9.4 mm), serving as the exit for the heated air towards the web, with the slot running in a substantially cross-machine direction over substantially the entire width of the web. In other embodiments, there may be a plurality of slots arranged next to each other or separated by a slight gap. The at least one slot is usually, though not essentially, continuous, and may be comprised of, for example, closely spaced holes. The HAK has a plenum to distribute and contain the heated air prior to its exiting the slot. The plenum pressure of the HAK is usually between about 1.0 and 12.0 inches of water (2 to 22 mmHg), and the HAK is positioned between about 0.25 and 10 inches and more preferably 0.75 to 3.0 inches (19 to 76 mm) above the forming wire. In a particular embodiment the HAK plenum's cross sectional area for cross-directional flow (i.e. the plenum cross sectional area in the machine direction) is at least twice the total slot exit area. Since the foraminous wire onto which spunbond polymer is formed generally moves at a high rate of speed, the time of exposure of any particular part of the web to the air discharged from the hot air knife is less a tenth of a second and generally about a hundredth of a second in contrast with the through air bonding process which has a much larger dwell time. The HAK process has a great range of variability and controllability of many factors such as air temperature, velocity, pressure, volume, slot or hole arrangement and size, and the distance from the HAK plenum to the web. The HAK is further described in U.S. patent application Ser. No. 08/362,328 to Arnold et al., filed Dec. 22, 1994 and commonly assigned.

As used herein, through-air bonding or "TAB" means a process of bonding a nonwoven bicomponent fiber web in which air which is sufficiently hot to melt one of the polymers of which the fibers of the web are made is forced through the web. The air velocity is between 100 and 500 feet per minute and the dwell time may be as long as 6 seconds. The melting and resolidification of the polymer provides the bonding. Through-air bonding has relatively restricted variability and since through-air bonding (TAB) requires the melting of at least one component to accomplish bonding, it is restricted to webs with two components like conjugate fibers or those which include a separate adhesive such as a low melting fiber or adhesive additive. In the through-air bonder, air having a temperature above the melting temperature of one component and below the melting temperature of another component is directed from a surrounding hood, through the web, and into a perforated roller supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

As used herein, the term "stitchbonded" means, for example, the stitching of a material in accordance with U.S. Pat. No. 4,891,957 to Strack et al. or U.S. Pat. No. 4,631,933 to Carey, Jr.

As used herein, "ultrasonic bonding" means a process performed, for example, by passing the fabric between a sonic horn and anvil roll as illustrated in U.S. Pat. No. 4,374,888 to Bornslaeger.

As used herein "thermal point bonding" involves passing a fabric or web of fibers to be bonded between a heated calender roll and an anvil roll. The calender roll is usually, though not always, patterned in some way so that areas of the fabric are unbonded, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

Figure 2:
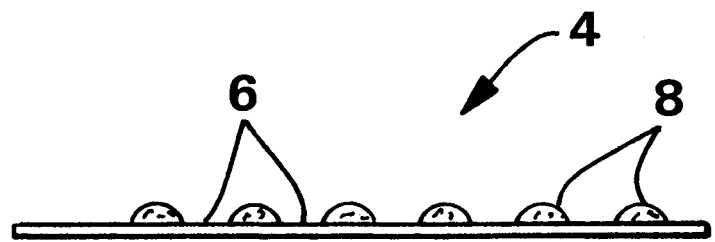
FIG. 2 is a cross-sectional side view of the pattern-unbonded nonwoven fabric of FIG. 1.

As used herein "pattern unbonded" or interchangeably "point unbonded" or "PUB", means a fabric pattern having continuous bonded areas defining a plurality of discrete unbonded areas. The fibers or filaments within the discrete unbonded areas are dimensionally stabilized by the continuous bonded areas that encircle or surround each unbonded area, such that no support or backing layer of film or adhesive is required. The unbonded areas are specifically designed to afford spaces between fibers or filaments within the unbonded areas. A suitable process for forming the pattern-unbonded nonwoven material of this invention includes providing a nonwoven fabric or web, providing opposedly positioned first and second calender rolls and defining a nip therebetween, with at least one of said rolls being heated and having a bonding pattern on its outermost surface comprising a continuous pattern of land areas defining a plurality of discrete openings, apertures or holes, and passing the nonwoven fabric or web within the nip formed by said rolls. Each of the openings in said roll or rolls defined by the continuous land areas forms a discrete unbonded area in at least one surface of the nonwoven fabric or web in which the fibers or filaments of the web are substantially or completely unbonded. Stated alternatively, the continuous pattern of land areas in said roll or rolls forms a continuous pattern of bonded areas that define a plurality of discrete unbonded areas on at least one surface of said nonwoven fabric or web. Alternative embodiments of the aforesaid process includes pre-bonding the nonwoven fabric or web before passing the fabric or web within the nip formed by the calender rolls, or providing multiple nonwoven webs to form a pattern-unbonded laminate. PUB fabrics are disclosed in U.S. patent application Ser. No. 08/754,419, commonly assigned and are shown in FIGS. 1 and 2 where continuous bonded areas 6 define a plurality of discrete, dimensionally-stabilized unbonded areas 8 in the nonwoven fabric 4.

Alternative applications in which PUB fabric may be used include those having film applied during the formation of the PUB fabric where the film will provide a liquid barrier so that it may be used as a clothlike outercover for a personal care product.

"Controlled spaces" refers to areas in a fabric which provide channels or troughs through which liquid may move. Examples include the bonded areas of PUB fabric, embossed areas of other nonwoven fabrics, and the valleys of ribbed patterned fabric like corduroy.

"Personal care product" means diapers, training pants, absorbent underpants, adult incontinence products, and feminine hygiene products.

Test Methods

Intake test

This test measures the liquid runover and run-through of a material.

Figure 3:
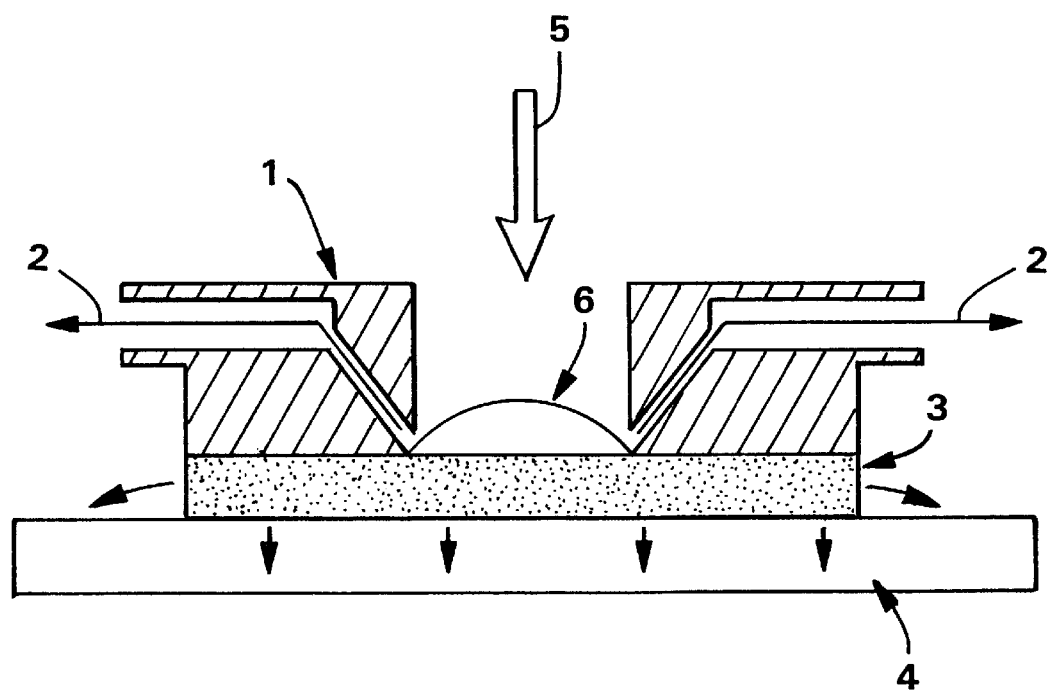
FIG. 3 is a schematic drawing for the intake test.

As shown in FIG. 3 this test uses a head assembly 1 which contains vacuum ports 2 which remove nunover liquid, i.e. liquid which travels to the end of the 3 inch diameter (76 mm) sample 3 without passing through it. The amount of vacuum is set to 5 inches of water below atmospheric pressure (about 750 mmHg absolute). The sample 3 sits on a porous sintered glass plate 4 which simulates an "ideal absorbent". The porous plate is calibrated by placing it horizontally in a funnel which drains through tubing into a beaker on a scale, filling the tubing and funnel assembly to a point above the porous plate with saline solution, and raising or lowering the funnel in relation to the scale in order to arrive at a porous plate pass-through rate of about 5 ml/s. The runthrough amount and the runover amount are separately gathered on scales, initially set to zero, for 30 seconds during the test.

An insult is delivered perpendicularly to the sample 3 through a 2.5 mm diameter circular opening 5 positioned 50 mm above the center of the sample at a rate of 5ml/s for a total of 50 ml of liquid and generally forms a bubble or pool 6. The liquid used is a saline solution having 0.9 weight percent sodium chloride. The amounts which runover (through the vacuum ports 2) and run through the porous plate 4 are measured by weight.

Runover and run-through add up to the total amount insulted so generally only one number is reported per test. In the results below, runover is reported in grams. A runover/runthrough percentage ratio is also reported where the runover amount is divided by the runthrough amount and multiplied by 100.

Vertical Wicking Test

A sample strip of material approximately 2 inches (5 cm) by 15 inches (38 cm) is placed vertically such that when the sample strip is positioned above a liquid reservoir at the beginning of the test, the bottom of the sample strip will just touch the liquid surface. The liquid used is a 8.5 g/l saline solution. The relative humidity should be maintained at about 90 to about 98 percent during the evaluation. Capillary tension in materials not containing superabsorbents is measured simply by the equilibrium vertical wicking height of a 8.5 g/l saline solution after 30 minutes and reported in centimeters.

Detailed Description

In personal care products, a liner is sometimes referred to as a bodyside liner or topsheet and may be adjacent a surge material. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

A surge layer is most typically interposed between and in intimate, liquid communicating contact with the bodyside liner and another layer such as a distribution or retention layer in a personal care product. The surge layer is generally subjacent the inner (unexposed) surface of a bodyside liner. To further enhance liquid transfer, it can be desirable to attach the upper and/or lower surfaces of the surge layer to the liner and the distribution layer, respectively. Suitable conventional attachment techniques may be utilized, including without limitation, adhesive bonding (using water-based, solvent-based and thermally activated adhesives), thermal bonding, ultrasonic bonding, needling and pin aperturing, as well as combinations of the foregoing or other appropriate attachment methods. If, for example, the surge layer is adhesively bonded to the bodyside liner, the amount of adhesive add-on should be sufficient to provide the desired level(s) of bonding, without excessively restricting the flow of liquid from the liner into the surge layer.

Retention materials are typically cellulosic materials or superabsorbents or mixtures thereof. Such materials are usually designed to quickly absorb liquids and hold them, usually without release. Superabsorbents are commercially available from a number of manufacturers including The Dow Chemical Company of Midland, Mich. and Stockhausen GmbH.

The backsheet of a personal care product is sometimes referred to as the outer cover and is the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the diaper.

Liner development has focused primarily on fluid strikethrough by providing durable treatments for multiple insult performance versus fluid management. Fluid management requires a liner with high permeability, z-directional fiber orientation (to promote z-directional wicking) and a surface topography capable of distributing the fluid under the liner resulting in greater product utilization. Such a structure should result in a high permeability interface capable of improved fluid intake and distribution. Disclosed is a liner that has a built in high permeability interface that directs fluid away from the entry point and distributes the liquid to the rest of the system. It is believed that this is accomplished by providing controlled spaces in the liner structure where the structures have permeabilities higher than, and preferably more than twice, the succeeding layer. The liquid pressure due to fluid momentum is believed to force a significant portion of the fluid to these controlled spaces which can either be uniform or channeled to direct the flow in a particular direction. Fabric having these controlled spaces should have a capillary tension according to the vertical wicking test of greater than 0.5 cm hydrostatic tension.

The inventors have found that a relatively simple structure, provided in the proper orientation, yields surprisingly improved results over similar webs without such orientation. The fabric of this invention intakes an insult with very little runoff and spreads the insult quite quickly. Such an absorbent nonwoven material is useful as a liner, a surge material, and in diverse applications such as filtration of water.

One type of fabric suitable for use in this invention is a nonwoven web which has been needled to orient the fibers and thereby improve permeability and thereafter embossed to provide the controlled spaces. The nonwoven web may be a bonded carded web. Another type of fabric suitable for this invention is a point unbonded fabric as defined above where the bonded areas serve as the controlled spaces. In any suitable fabric the controlled spaces must be on the side away from a wearer in order to provide spreading of the insult away from the skin of the wearer.

Three structures were tested to determine their intake speed and distribution. These structures, while superficially quite similar, produced different results, with the results of the structure of this invention being particularly startling. The three structures were a thermally point bonded polypropylene spunbond web (structure 1), a through-air bonded (TAB) conjugate fiber web (structure 2) and a point unbonded (PUB) conjugate fiber web (structure 3). All three structures were treated for wettability. Details of web contraction and testing follow.

Structure 1

This material was a thermally point bonded polypropylene nonwoven web made by the spunbond process. The fibers were produced at a rate of about 0.9 grams/hole/minute (ghm) and drawn with cold air. After passing through a slightly heated compaction roll, the web was transferred to a nip between two heated steel rolls, one a smooth anvil roll and the other an engraved roll with the EHP bond pattern with about 17 percent bond area. Average fiber size was about 4.9 denier and average web basis weight was about 19 gsm.

Structure 2

This structure was a through-air bonded (TAB) side-by-side conjugate fiber of polypropylene and linear low density polyethylene in equal proportions, each with about 2 weight percent of titanium dioxide pigment. The polypropylene was Escorene® PD 3445 polypropylene from Exxon Chemical Co. of Houston, Tex. and the polyethylene was Aspun® 6811A from the Dow Chemical Co. of Midland Mich. Polymer throughput was about 1.2 ghm. The fibers were drawn with hot air to activate latent crimp according to U.S. Pat. No. 5,382,400 and the material was passed through a hot air knife (HAK) to consolidate it for further processing. The fabric was through air bonded at about 124° C. and a pressure differential of about 100 Pascals. Average fiber size was about 5.2 denier and web basis weight was about 22.5 gsm.

Structure 3

Figure 6:
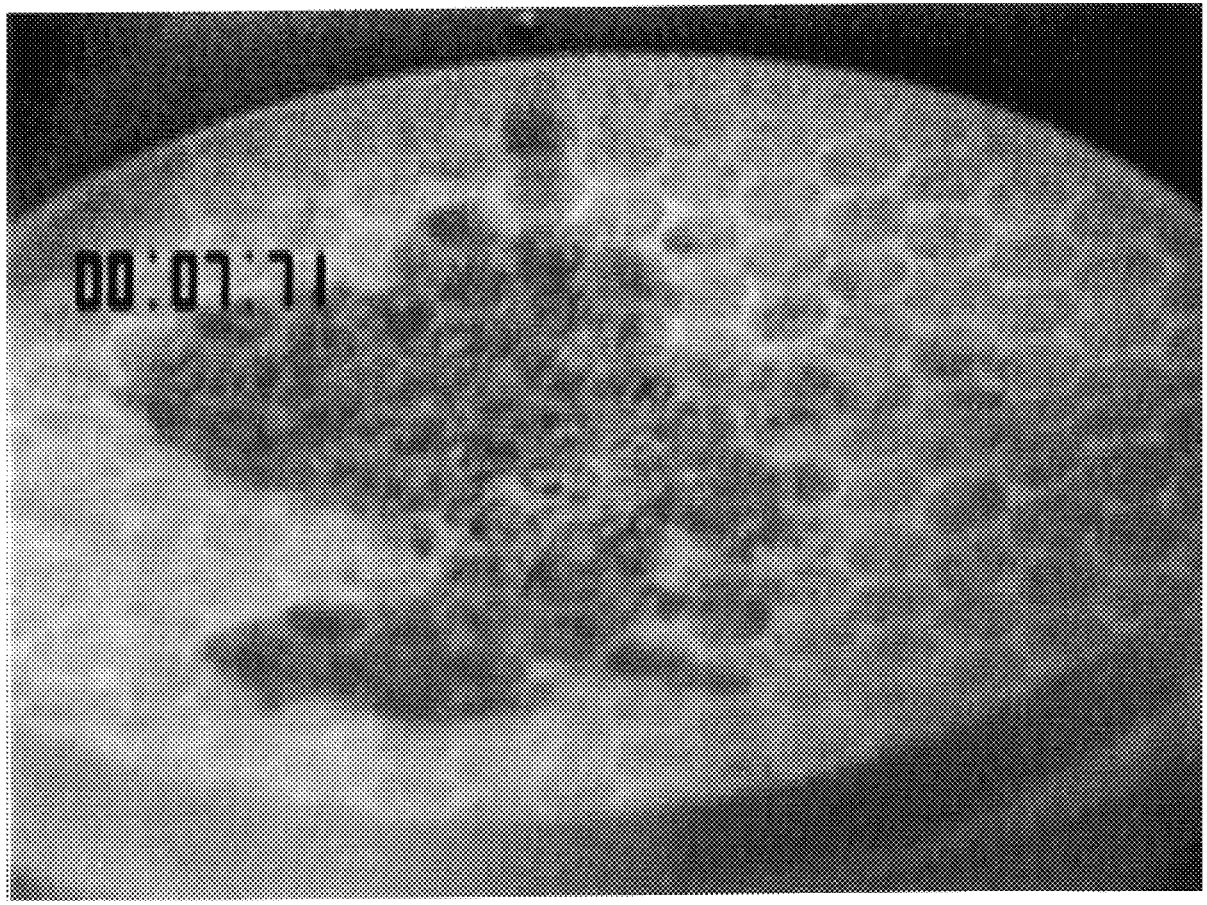
FIG. 6 is a picture of the spread of an insult on the PUB fabric of structure 3 after about 8 seconds, where the insult has been fully absorbed and spread.

This structure was almost identical to structure 2 except that instead of through-air bonding, the web was bonded between two heated steel rolls. One steel roll was a smooth anvil roll and the other was an engraved patterned roll with a circle PUB pattern with about 30 percent bond area. This structure 3 was produced using the same polymers as structure 2 and at a throughput of about 1.3 ghm, drawn with hot air to activate the latent crimp, and had a basis weight of about 22.5 gsm and denier of about 4.9. This structure was tested with the bumps produced by the PUB process downward. FIG. 6 shows the bumps downward as well.

Wettability treatment

All three structures were treated in the same manner with a solution of 42 g of Ahcovel® Base N-62 surfactant, which is a blend of about 50 weight percent sorbitan mono-oleate and about 50 weight percent hydrogenated ethoxylated castor oil at 100 percent solids supplied by ICI Chemicals, 4.6 g Glucopons® UP-220, an alkyl polyglycoside with a C8-10 chain at 60 percent solids supplied by Henkel Chemicals, and 40 g hexanol diluted with warm water to 8 liters and stirred thoroughly. Eight foot (2.4 m) long sheets of each web were soaked in this solution and wrung out to leave a total solution add-on of about 60 percent of the original dry weight of the web. The webs were then air dried, leaving a 0.3 to 0.4 weight percent dried residue of the aqueous solution on the web.

It should be noted that wettability treatments will vary depending on the polymers chosen. Any treatment, external or internal, known to those skilled in the art to produce hydrophilic fibers, may be used. The important issue is that the fibers are, or become hydrophilic.

All three structures were tested according to the intake test. The results are given below for a first, second and third insult (down) for four pieces of each fabric (across).

| Insult | Intake test results | | | | average |
|---|---|---|---|---|---|
| Structure 1 | | | | | |
| 1 | 3.14 | 1.5 | 2.05 | 2.93 | 2.41 |
| 2 | 2.86 | 2.45 | 1.65 | 2.89 | 2.46 |
| 3 | 2.44 | 1.52 | 1.58 | 1.56 | 1.78 |
| | | | | average | 2.21 |
| | | | | std. Dev. | 0.64 |
| | | | average runover/runthrough percentage ratio: 4.6 | | |
| Structure 2 | | | | | |
| 1 | 1.07 | 2.06 | 2.22 | 1.29 | 1.66 |
| 2 | 0.41 | 3.85 | 1.04 | 2.21 | 1.88 |
| 3 | 0.51 | 1.97 | 2.63 | 1.45 | 1.64 |
| | | | | average | 1.73 |
| | | | | std. Dev. | 0.97 |
| | | | average runover/runthrough percentage ratio: 3.6 | | |
| Structure 3 | | | | | |
| 1 | 0.51 | 0.88 | 0 | 0.57 | 0.49 |
| 2 | 0 | 0.67 | 0 | 0.74 | 0.35 |
| 3 | 0.29 | 0.21 | 0.38 | 0.56 | 0.36 |
| | | | | average | 0.40 |
| | | | | std. Dev. | 0.30 |
| | | | average runover/runthrough percentage ratio: 0.8 | | |

Figure 4:
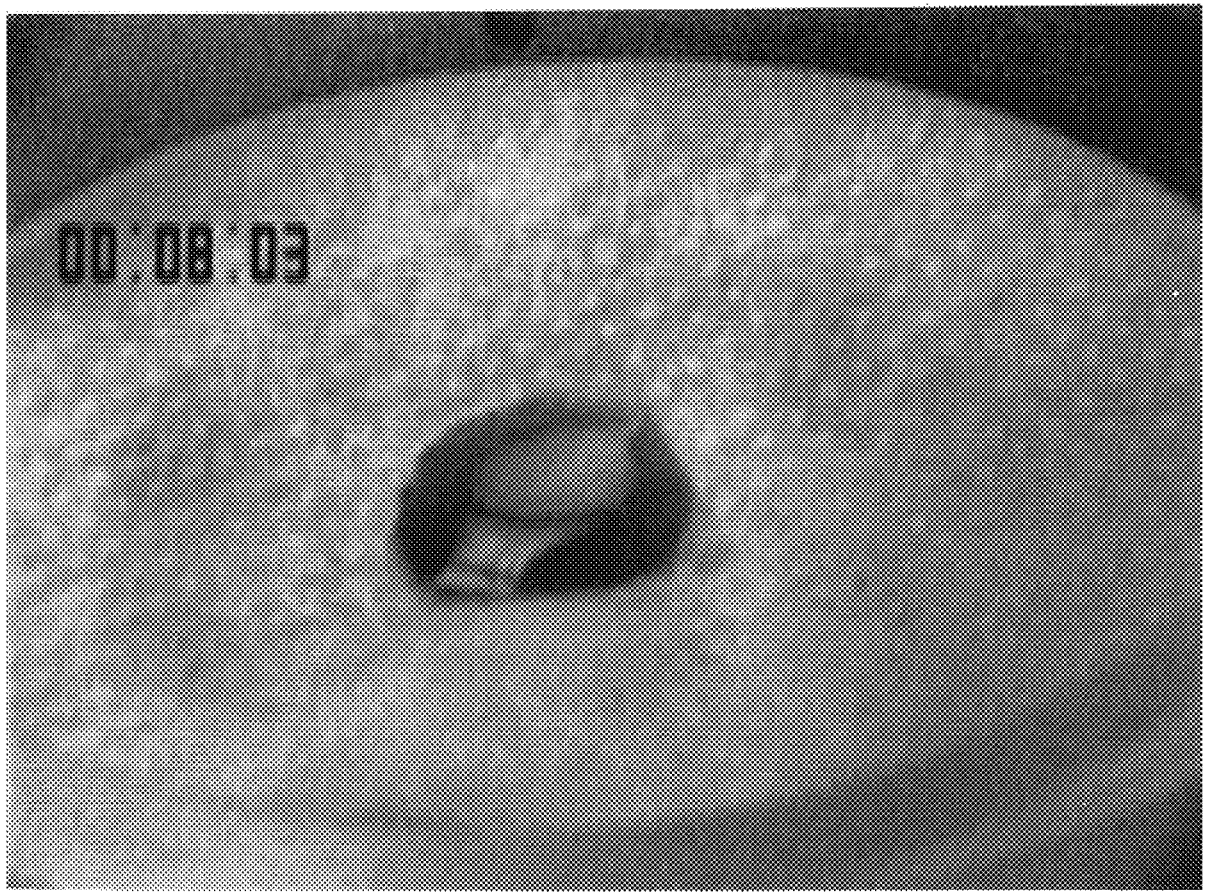
FIG. 4 is a picture of the spread of an insult on the polypropylene spunbond fabric of structure 1 after about 8 seconds, where the insult is still beaded up on the surface of the fabric.
Figure 5:
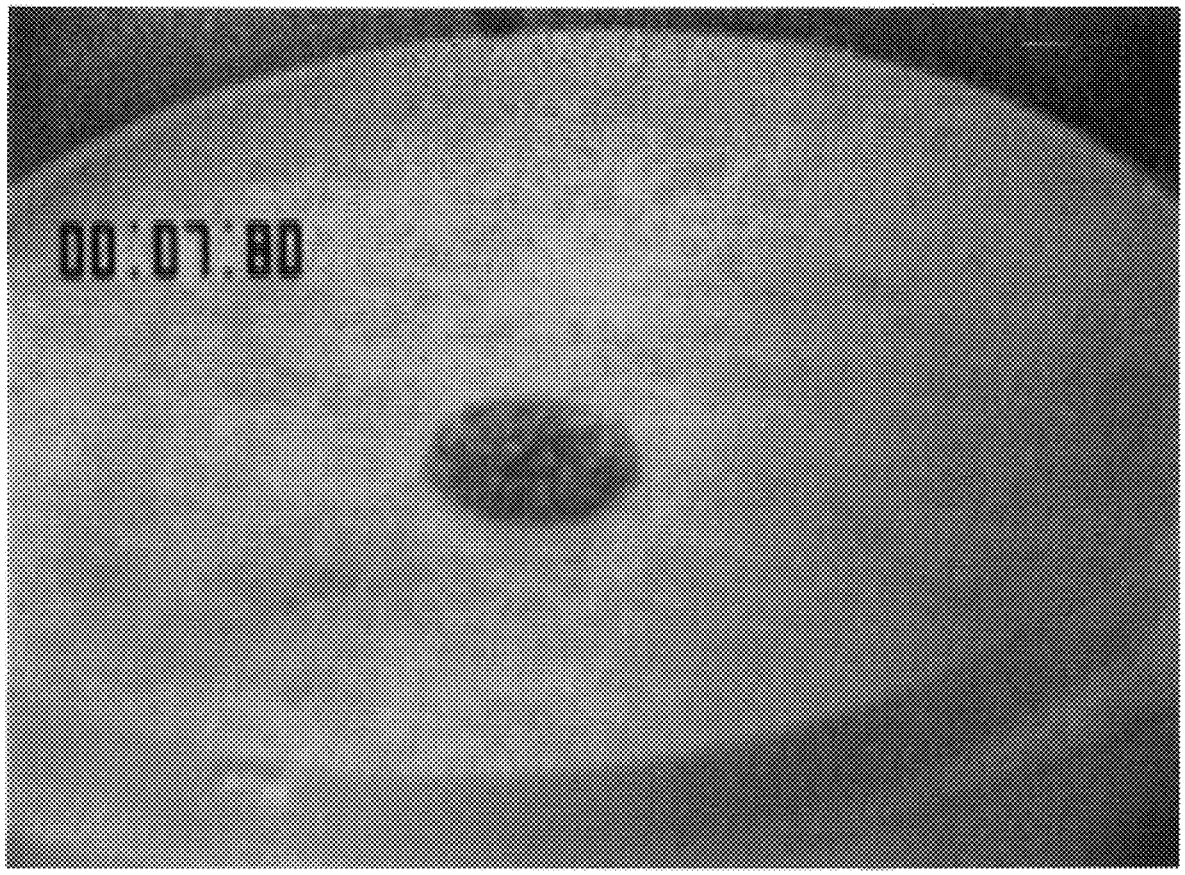
FIG. 5 is a picture of the spread of an insult on the TAB fabric of structure 2 after about 8 seconds where the insult has just been absorbed.

The surprisingly better results realized with the PUB fabric in comparison with the almost identical TAB fabric and polypropylene spunbond fabric as shown in the test results may also be seen quite clearly in FIGS. 4, 5 and 6. These figures show the spread of an identical insult on the fabric after about 8 seconds. The PUB fabric picture (FIG. 6) visually illustrates how quickly and how far the PUB fabric intakes and distributes an insult in comparison with the other similar webs.

Fabrics of this invention will generally have a runover to run-through percentage ratio of less than 1.5 and more preferably less than 1. These fabrics will also spread an insult, as shown in the Figures, at least twice as far in 8 seconds as a similar fabric without the controlled spaces of this invention.

Disclosed is a liner that has a built in high permeability interface that directs fluid away from the entry point and distributes the liquid to the rest of the system. It is believed that this is accomplished by providing controlled spaces in the liner structure that have permeabilities higher than the succeeding layer. The liquid pressure due to fluid momentum is believed to force a significant portion of the fluid to the higher permeability spaces. These controlled spaces can either be uniform or channeled to direct the flow in a particular direction.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. An absorbent nonwoven material comprising a wettable web of fibers of at most 40 microns in diameter wherein said web has controlled spaces on a surface away from a wearer and which accepts a liquid insult of 50 ml with a runover/run-through percentage ratio of less than 1.5.

2. A liner for personal care products comprising the material of claim 1.

3. A surge layer for personal care products comprising the material of claim 1.

4. A personal care product selected from the group consisting of diapers, training pants, absorbent underpants, adult incontinence products and feminine hygiene products comprising the material of claim 1.

5. The product of claim 4 wherein said personal care product is a feminine hygiene product.

6. The product of claim 4 wherein said personal care product is an adult incontinence product.

7. The product of claim 4 wherein said personal care product is a diaper.

8. The diaper of claim 7 having a crotch width of at most 7.6 cm.

9. The absorbent material of claim 1 having a runover/runthrough percentage ratio of less than 1.

10. The absorbent material of claim 1 wherein an insult will spread at least twice as far in 8 seconds as a similar fabric without said controlled spaces.

* * * * *